United States Patent [19]

English

[11] Patent Number: 4,947,510
[45] Date of Patent: Aug. 14, 1990

[54] VACUUM BOX FOR COLLECTING SMALL PARTICLES

[76] Inventor: Philip C. English, Rt. 1 Box 136, Fredericksburg, Va. 22401

[21] Appl. No.: 342,273

[22] Filed: Apr. 21, 1989

[51] Int. Cl.$^5$ .............................................. A47L 5/38
[52] U.S. Cl. ........................................ 15/310; 15/301; 15/303; 55/DIG. 18; 98/115.1
[58] Field of Search .................... 15/301, 310, 303; 55/385 A, DIG. 18; 98/115.1

[56] References Cited

U.S. PATENT DOCUMENTS

| | | | |
|---|---|---|---|
| 3,295,298 | 1/1967 | Mackey | 15/310 X |
| 3,880,061 | 4/1975 | Hensiek et al. | 98/115.1 |
| 4,490,881 | 1/1985 | Schmidt | 15/301 |
| 4,594,747 | 6/1986 | Dempsey | 15/301 |
| 4,596,060 | 6/1286 | Schmidt et al. | 15/301 X |
| 4,607,413 | 8/1986 | Schmidt et al. | 15/301 |
| 4,647,295 | 3/1987 | Christ | 15/301 X |

Primary Examiner—Chris K. Moore
Attorney, Agent, or Firm—James L. Sherman

[57] ABSTRACT

A vacuum box is for collecting small particles or the like. the vacuum box includes a cabinet having a front, a rear and a hollow interior. The front of the cabinet includes a substantially horizontal working surface at a lower region thereof. The working surface includes an air inlet opening therethrough. A motor and fan are disposed within the hollow interior of the cabinet at the rear thereof for the discharge of air from the hollow interior of the cabinet. A collection compartment is disposed below the working surface and the air inlet opening therethrough with a rear portion of the collection compartment being disposed within the interior of the cabinet. A filter is disposed within the interior of the cabinet between the collection compartment and the fan. The fan causes the air including the particles produced at the working surface to be drawn downwardly through the air inlet opening into the collection compartment, upwardly from the rear portion of the collection compartment, and through the filter. A substantial portion of the particles remain in the collection compartment and a remaining portion of the particles are collected on the filter. The collecting compartment is accessible for selectively removing the substantial portion of the particles from the collecting compartment.

9 Claims, 1 Drawing Sheet

VACUUM BOX FOR COLLECTING SMALL PARTICLES

BACKGROUND OF THE INVENTION

1. Field of the Invention

This invention relates to a vacuum box for collecting small particles such as wood chips or shavings but may also be utilized for the collection of dental scrapings and dust or small metal fragments resulting from the fabrication of gold products or the like.

2. Description of the Prior Art

In the carving field, there are presently existing a number of vacuum boxes which are intended to collect small wood shavings or sawdust in order to reduce the contamination of the surrounding area or to the air.

One such vacuum box utilizes a hooded cofiguration with an exposed filter in which air is drawn through the filter for the collection of the dust thereon. While such a configuration may prevent general disposition of the dust in the air, the exposed side of the filter could inadvertently become a source of sawdust if it is accidently dislodged or removed prior to proper disposition. Additionally, if the pieces of wood produced by the carving are relatively large, there is no guarantee that they will properly adhere to the filter surface.

Another large vacuum box used in the carving field includes a large evacuated container in which the entire lower region of the container is intended for the collection of wood particles or dust. A working surface for this large vacuum box includes a screen for pulling the particles into the interior of the vacuum box. Once the particles are inside the vacuum box, they may fall to the enlarged lower region for eventual removal. Air inside the vacuum box is evacuated through an upper region of the box and discharged out the rear of the vacuum box. However, collection of the particles in this manner can be quite dangerous. Collection of wood particles in the lower region of such a large box has resulted in a fire hazard since small sparks entering the screened working area could deposit in the collection of dust particles in the lower region of the large vacuum box. Since such a spark could create a fire in the lower region of the large vacuum box, the operator may not even be aware of its existence until the fire is out of control.

U.S. Pat. No. 4,047,913 discloses a dust collector for dental technicians. However, the configuration disclosed therein, while appearing similar to that of the present invention, includes a relatively complicated double-screened area which is exposed to the operator. Air passing through the screen goes through a fan which ultimately discharges to yet another screen configuration for the collection of fine dust particles. However, this configuration, similar to that mentioned above, allows major particles to be left on an exposed surface for possible loss to the atmosphere or surroundings. Still further, including a major filter after the fan leaves the fan exposed to small particles which are being forced therethrough. If such a device was used in the carving field, the collection of sawdust around the motor of the fan could, as mentioned above, result in a fire hazard.

U.S. Pat. No. 2,602,417 discloses a dusting cabinet used in the preparation of printing plates or the like. Again, such a configuration employs a large cabinet and causes the particles or substance therein to be drawn to a lower region thereof. Collection of the lower region in filters could again, if used, for example, in the carving field, result in a collection of dust subject to combustion. Collection in the lower region in this manner would make discovery by the operator less likely and eventual suppression of the combustion more difficult.

A number of other patents disclose more complicated exhaust or collecting devices which have particular application in specific work-related environments. U.S. Pat. No. 1,902,211 discloses a hair collecting device which is used in barber shops to remove hair from barbers' aprons or the like. U.S. Pat. No. 1,934,808 discloses a single-draft fume hood for use in chemical laboratories and other places where more or less noxious or disagreeable fumes are developed in the course of chemical operations. U.S. Pat. No. 1,977,386 discloses a work hood to cover articles or workpieces which is connected to a central vacuuming and collection system for the entire shop area. U.S. Pat. No. 4,637,301 is directed to a contamination control work station for use when working on radioactive or other toxic or hazardous materials to prevent the release of contaminated and toxic gases and particles to the atmosphere.

OBJECTS OF THE INVENTION

It is therefore an object of the invention to provide a vacuum box for collecting small particles which is simple, reliable and relatively inexpensive to provide.

It is another object of the invention to provide such a vacuum box in which the collection of the particles is facilitated in a manner which reduces the likelihood of undesired combustion thereof.

It is a further object of the invention to provide such a vacuum box which insures that all particles will eventually be entrapped without being collected on the motor or the like so that the particles can be subsequently removed and/or collected when desired.

SUMMARY OF THE INVENTION

These and other objects of the invention are provided in a preferred embodiment thereof including a vacuum box for collecting small particles or the like. The vacuum box includes a cabinet having a front, a rear and a hollow interior. The front of the cabinet includes a substantially horizontal working surface at a lower region thereof. The working surface includes an air inlet opening therethrough. A motor and fan are disposed within the hollow interior of the cabinet at the rear thereof for the discharge of air from the hollow interior of the cabinet. A collection compartment is disposed below the working surface and the air inlet opening therethrough with a rear portion of the collection compartment being disposed within the interior of the cabinet. A filter is disposed within the interior of the cabinet between the collection compartment and the fan. The fan causes the air including the particles produced at the working surface to be drawn downwardly through the air inlet opening into the collection compartment, upwardly from the rear portion of the collection compartment, and through the filter. A substantial portion of the particles remain in the collection compartment and a remaining portion of the particles are collected on the filter. The collecting compartment is accessible for selectively removing the substantial portion of the particles from the collecting compartment.

DESCRIPTION OF THE PREFERRED EMBODIMENTS

Figure 1:
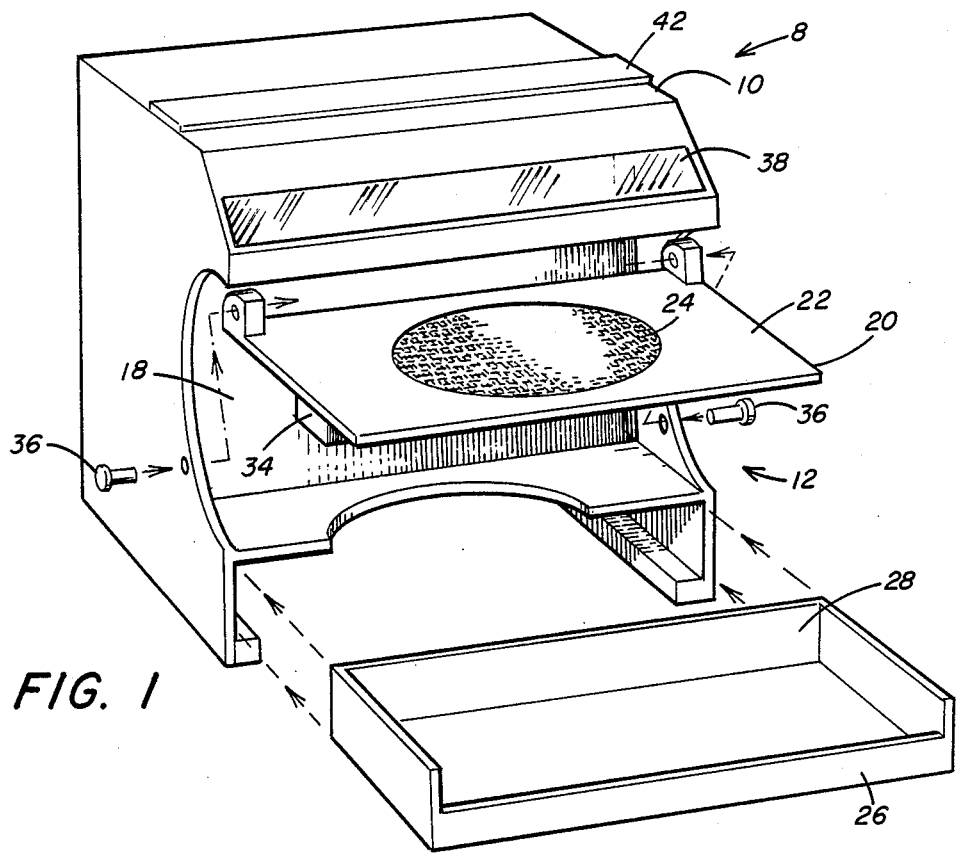
FIG. 1 is an exploded perspective view of the preferred vacuum box including a relationship of the various components thereof.
Figure 2:
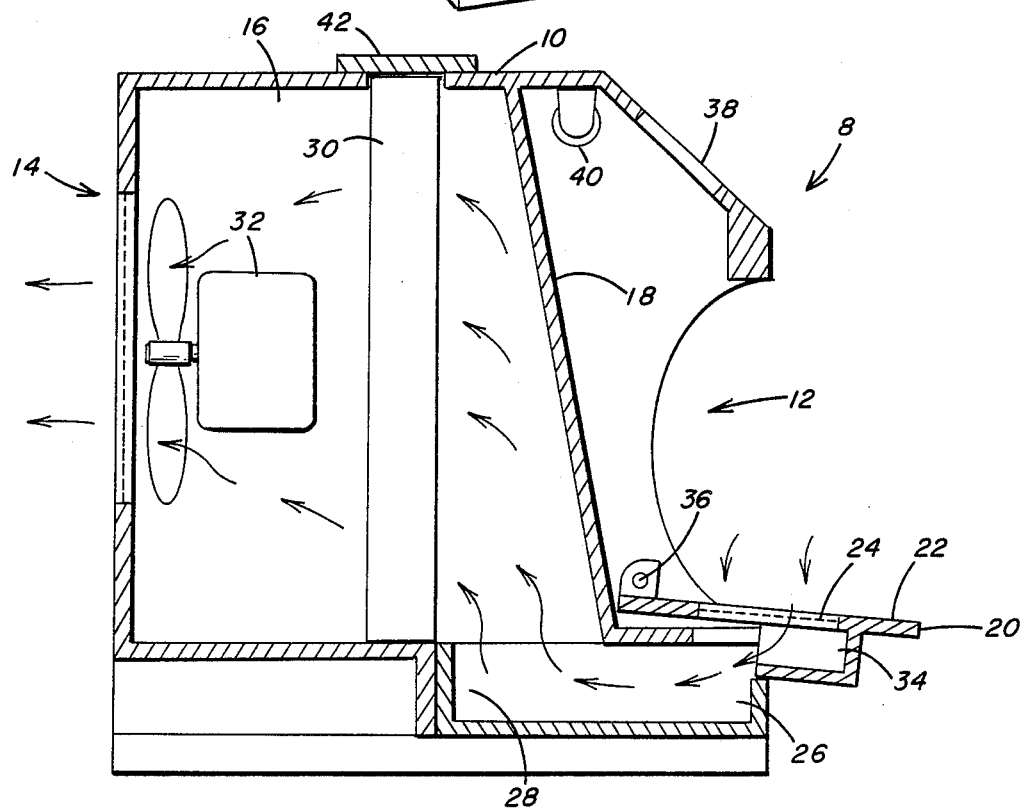
FIG. 2 is a schematic sectional side view of the preferred vacuum box including various features of the invention.

As seen in FIGS. 1 and 2, the preferred vacuum box 8 is for the collection of small particles or the like which can be produced by, for example, carving wood products. A cabinet 10 of the vacuum box 8 includes a front 12, a rear 14 and a hollow interior 16. The front 12 is generally hooded at the top and sides of a front wall 18. At the lower region of the front wall 18 is disposed a generally horizontal working table 20. The horizontal working table 20 includes a working surface 22 with an air inlet or opening 24 disposed centrally therein. The air inlet 24 includes a screen or mesh covering to prevent large articles from falling through the working surface 22 but is not intended to collect dust or any other matter.

Beneath the working table 20 is a collection box 26 which serves as a compartment means for the collection of particles of the wood or the like created during carving. The rear end 28 of the collection box 26 is disposed within the interior 16 of the cabinet 10. Also within the interior of the cabinet 10 is a removable filter 30 which is intended to entrap particles or the like which remain in the air passing through the cabinet 10 after leaving the collection box 26.

In order to produce an air flow through the cabinet 10, a fan and motor means 32 are disposed within the interior 16 of the cabinet 10 at the rear thereof for the discharge of air being drawn through the hollow interior 16 of the cabinet 10.

During normal operation, as one is working at the working surface 22 with the fan 32 in operation, small chips and particles of wood or the like will be drawn downwardly through the air inlet or opening 24 into the front region of the collection box 26. As the air passes through the collection box 26 toward the rear 28 thereof, the particles are propelled rearwardly. The air, however, is directed upwardly into the interior of the cabinet 10 at the front side of the filter 30. This change in direction of the air causes most of the particles of wood or the like to be collected and retained within the collection box 26. However, as the upwardly moving air is then drawn through the filter 30 by the fan 32, additional particles still entrapped in the air will be properly collected on the filter 30.

The collection of particles in this manner tends to prevent any of the particles from being passed to the fan or the motor thereof which could, in the case of wood, create a fire hazard. Clearly, such a collection of wood or other material at the motor could also reduce the operating efficiency of the motor. The preferred method of collecting particles according to the invention prevents them from all being entrapped in the filter which could have an adverse effect on the ability of the fan to properly and continually draw the air through the cabinet 10 and could thus decrease the efficiency or effectiveness of the vacuum box 8 and its primary purpose of being able to collect the particles.

Accordingly, the use of the collecting box 26 insures that a substantial portion of the particles will be retained therein rather than being directed to the filter. In order to be able to remove the particles entrapped within the collection box 26, the collection box 26 is capable of being removed from the front 12 of the cabinet 10. The preferred collection box 26 is mounted in a drawer fashion for easy removal. In order to provide proper sealing of and alignment with the top of the collection box 26, the working table 20 is disposed closely over the forward end of the collection box 26 and even includes a forward compartment 34 to insure that the air will be properly directed toward the collection box 26.

The preferred working table 20 is removably mounted above the collection box 26 by removable pins 36. However, it would also be possible for the working table 20 to be simply hinged at the pins 36 or the like for rotation in order to be lifted above the collection box 26 for its removal. Still further, although not preferred, it would be possible for the working table 20 to be lifted or removed in the manner described above so that a vacuum cleaner or the like could be inserted into the collection box 26 for subsequent removal of the particles entrapped therein without the box 26 being actually removed from the cabinet 10.

Several other features are included in the preferred vacuum box 8 for facilitating the carving of objects or the like at the working surface 22. Part of the hooding at the front 12 of the cabinet 10 includes a clear plexiglass covering 38 for viewing of articles thereunder. Still further, a light 40 can be installed under the hood in order to provide additional lighting for the carving operation.

In a preferred vacuum box 8, the filter 30 is a standard 16"×25"×2" filter with the interior of the cabinet 10 being specifically sized to accommodate these existing filters 30. The simple manner of installing the filter 30 facilitates not only a reliable operation for the direction of the air therethrough but also facilitates easy removal for subsequent cleaning by the removal of a cover 42.

While the preferred vacuum box 8 is primarily intended for the collection of sawdust, wood chips or the like during a carving operation, it should be recognized that some of the features which make the vacuum box 8 attractive for such a use are also applicable for use by, for example, a dental technician. A dental technician could use the working surface 22 in the same manner as could a carver with the undesired particles again being primarily retained within the collection box 26 so that subsequent removal, cleaning or disposition of the filter 30 would not be as frequently required.

More significantly, the preferred vacuum box 8 could be utilized for the carving or grinding of gold by jewelry makers or the like and could serve the additional function of providing a proper means for retaining the gold particles or chips for future use. If gold is ground at the working surface 20, the gold particles would, again, primarily collect in the collection box 26 at the rear 28 thereof. Because of the weight of gold, it would be expected that more particles would be entrapped in the collection box 26. Nevertheless, some particles may be directed upwardly into the interior of the cavity 10 for passage through the filter 30. Again, the filter 30 would be expected to collect all the remaining particles entrapped in the air. However, when jewelry work produces small particles of gold in this manner, the gold particles are subsequently retrieved for melting and reuse. The gold in the collection box 26 could be easily recovered and the gold entrapped in the filter 30 would normally be recovered by heating and burning the filter 30 to collect the gold entrapped therein.

From the discussion of the preferred vacuum box 8 provided hereinabove, it should be clear that various alterations could be made to the preferred vacuum box without departing from the scope of the invention as claimed.

What is claimed is:

1. A vacuum box for collecting small particles or the like comprising:

a cabinet having a front, a rear and a hollow interior;

said front of said cabinet including a substantially horizontal working surface at a lower region thereof;

said working surface including air inlet means therethrough;

fan means disposed at said rear of said cabinet for the discharge of air from said hollow interior of said cabinet;

collection compartment means disposed below said working surface and said air inlet means therethrough with a rear portion of said collection compartment means being disposed within said interior of said cabinet;

filter means disposed within said interior of said cabinet between said collection compartment means and said fan means;

said fan means causing the air including the particles produced at said working surface to be drawn downwardly through said air inlet means into said collection compartment means, upwardly from said rear portion of said collection compartment means, and through said filter means;

a substantial portion of the particles remaining in said collection compartment means and a remaining portion of the particles being collected on said filter means; and means for selectively removing the substantial portion of the particles from said collecting compartment means.

2. The vacuum box according to claim 1, wherein said means for selectively removing the substantial portion of the particles includes said collection compartment means being removable from said front of said cabinet.

3. The vacuum box according to claim 2, wherein said working surface is on a working table and said working table is capable of being upwardly displaced for allowing the removal of said collection compartment means from said front of said cabinet.

4. The vacuum box according to claim 1, wherein said working surface is on a working table and said working table is capable of being selectively displaced upwardly of said collection compartment means for allowing access to said collection compartment means.

5. The vacuum box according to claim 4, further including means for selectively removing said working table from said front of said cabinet.

6. The vacuum box according to claim 1, wherein said air inlet means is a screened opening centrally disposed in said working surface.

7. The vacuum box according to claim 1, wherein said filter means extends substantially across said interior of said cabinet.

8. The vacuum box according to claim 7, further including means for removing said filter means from said interior of said cabinet.

9. The vacuum box according to claim 1, wherein said front of said cabinet is substantially hooded to direct the air and the particles at said working surface toward said air inlet means.

* * * * *